(12) United States Patent
Linares (10) Patent No.: US 11,432,937 B1
(45) Date of Patent: Sep. 6, 2022

(54) EXPANDABLE SPINAL JACK FOR INSTALLATION BETWEEN UPPER AND LOWER SUCCEEDING SUPERIOR ARTICULAR PROCESSES

(71) Applicant: Linares Medical Devices, LLC, Auburn Hills, MI (US)

(72) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 0 days.

(21) Appl. No.: 17/516,885

(22) Filed: Nov. 2, 2021

(51) Int. Cl.
*A61F 2/44* (2006.01)
*A61F 2/30* (2006.01)

(52) U.S. Cl.
CPC ........ *A61F 2/4405* (2013.01); *A61F 2/30749* (2013.01); *A61F 2002/30014* (2013.01); *A61F 2002/3055* (2013.01); *A61F 2002/30143* (2013.01); *A61F 2002/30405* (2013.01); *A61F 2002/30525* (2013.01); *A61F 2002/30892* (2013.01)

(58) Field of Classification Search
CPC .. A61F 2/44; A61F 2/442; A61F 2/447; A61F 2/4455; A61F 2/46; A61F 2/4611; A61B 17/70; A61B 17/7067; A61B 17/7068
See application file for complete search history.

(56) References Cited

U.S. PATENT DOCUMENTS

| | | | |
|---|---|---|---|
| 8,574,267 B2 | 11/2013 | Linares | |
| 8,585,738 B2 | 11/2013 | Linares | |
| 8,613,758 B2 | 12/2013 | Linares | |
| 8,617,212 B2 | 12/2013 | Linares | |
| 8,623,056 B2 | 1/2014 | Linares | |
| 8,728,123 B2 | 5/2014 | Bucci et al. | |
| 9,149,306 B2 * | 10/2015 | Zamani | A61B 17/7068 |
| 9,247,968 B2 | 2/2016 | Taber et al. | |
| 9,326,797 B2 | 5/2016 | Dinville et al. | |
| 9,561,060 B2 | 2/2017 | Taber et al. | |
| 9,775,718 B2 | 10/2017 | Taber et al. | |
| 9,913,667 B2 | 3/2018 | Dinville et al. | |
| 9,968,381 B2 | 5/2018 | Thalgott et al. | |
| 10,076,422 B2 | 9/2018 | Zappacosta et al. | |
| 10,398,478 B2 | 9/2019 | Ganter et al. | |
| 10,478,232 B2 | 11/2019 | Pool et al. | |
| 10,517,652 B2 | 12/2019 | Dinville et al. | |
| 10,543,024 B2 | 1/2020 | Lee et al. | |
| 10,695,189 B2 | 6/2020 | Li et al. | |
| 10,751,094 B2 | 8/2020 | Green et al. | |
| 10,792,078 B2 | 10/2020 | Smisson, III et al. | |
| 10,835,297 B2 | 11/2020 | Altarac et al. | |
| 11,065,040 B2 | 7/2021 | Zappacosta et al. | |
| 2009/0209965 A1 * | 8/2009 | Lewis | A61B 17/7065 606/90 |

(Continued)

*Primary Examiner* — Christopher J Beccia
(74) *Attorney, Agent, or Firm* — Dinsmore & Shohl LLP (57) ABSTRACT

A spinal jack adapted for installation between first and second vertebral processes, including first and second inter-expandable jack halves arranged between retracted and expanded positions. Each of the jack halves further includes gripping portions adapted for engaging the vertebral processes. A geared mechanism provides for expanding or retracting the jack halves in order to establish a corrected adjusted orientation between the processes.

12 Claims, 9 Drawing Sheets

(56) References Cited

U.S. PATENT DOCUMENTS

| | | |
|---|---|---|
| 2011/0184468 A1 | 7/2011 | Metcalf, Jr. et al. |
| 2011/0313467 A1 | 12/2011 | Youssef et al. |
| 2012/0004727 A1 | 1/2012 | Ben-Mokhtar et al. |
| 2012/0109205 A1 | 5/2012 | Mitchell et al. |
| 2012/0226314 A1 | 9/2012 | Chin et al. |
| 2012/0253393 A1 | 10/2012 | Fiorella |
| 2013/0103087 A1 | 4/2013 | Grizzard |
| 2013/0184754 A1* | 7/2013 | Taber ................. A61B 17/7061 606/279 |
| 2013/0197581 A1 | 8/2013 | Justis et al. |
| 2015/0164656 A1 | 6/2015 | Zappacosta et al. |
| 2015/0313650 A1 | 11/2015 | Taber et al. |
| 2015/0359640 A1 | 12/2015 | Taber et al. |
| 2016/0007983 A1* | 1/2016 | Frey ................... A61B 17/7077 606/86 A |
| 2016/0022324 A1 | 1/2016 | Yoon et al. |
| 2017/0319351 A1 | 11/2017 | Bechtel et al. |
| 2017/0333091 A1 | 11/2017 | Taber et al. |
| 2018/0078381 A1 | 3/2018 | Taber et al. |
| 2018/0263667 A1 | 9/2018 | Dinville et al. |
| 2019/0159812 A1 | 5/2019 | Zappacosta et al. |
| 2019/0201057 A1 | 7/2019 | Altarac et al. |
| 2020/0038071 A1 | 2/2020 | Pool et al. |
| 2020/0297392 A1 | 9/2020 | Zappacosta et al. |
| 2021/0052307 A1 | 2/2021 | Soo et al. |
| 2021/0169657 A1 | 6/2021 | Bechtel et al. |
| 2021/0204985 A1 | 7/2021 | Choi et al. |

* cited by examiner

EXPANDABLE SPINAL JACK FOR INSTALLATION BETWEEN UPPER AND LOWER SUCCEEDING SUPERIOR ARTICULAR PROCESSES

FIELD OF THE INVENTION

The present invention relates generally to spinal jacks for providing inter-vertebral support. More specifically, the present invention teaches an adjustable spinal jack for installation between superior articular processes of upper and lower succeeding vertebrae.

BACKGROUND OF THE INVENTION

Spinal jacks designs are known in the prior art for providing adjusted and secure positioning support between succeeding spinal vertebra. An examples of this is depicted in Linares U.S. Pat. No. 8,623,056.

SUMMARY OF THE PRESENT INVENTION

The present invention discloses a spinal jack adapted for installation between first and second vertebral processes, including first and second inter-expandable jack halves arranged between retracted and expanded positions. Each of the jack halves further includes gripping portions adapted for engaging the vertebral processes. A geared mechanism provides for expanding or retracting the jack halves in order to establish a corrected adjusted orientation between the processes.

In a first variant, a hex key rotatable driver actuates, via a bevel gear arrangement, a pair of laterally expandable slave gears supported upon a stationary shaft. A pair of extending support stems associated with one of the jack halves are provided and include inwardly stepped ratchet locations which abut the opposite outward faces of the slave gears in order to adjust a lateral separation between the jack halves. The spinal jack halves are further biased in an outward expanding direction.

In a second variant, a central body supports the outwardly displaceable spinal jack halves and includes a rotatable worm gear which in turn actuates a disk gear having both outer and inner coaxial arranged threads. These in turn mesh with threads configured in support stems associated with each of the jack halves and so that, upon actuating the worm gear to drive the disk gear, the spinal jack halves are caused to inter-displace in an outwardly expanding configuration.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

With reference to the attached illustrations, the present invention discloses a number of variants of an adjustable spinal jack for installation between superior articular processes of upper and lower succeeding vertebrae. A general representation of a selected jack is depicted generally at 10 in the perspective view of FIG. 1 and is understood to be positioned between upper and lower 4 successive superior articular processes (not shown) corresponding to upper and lower vertebrae.

As will be described in further detail with reference to the succeeding embodiments, the present invention provides an expandable spinal jack which overcomes many of the disadvantages of the prior art and provides an effective solution for stabilizing and fixing in position a given orientation established between the succeeding vertebrae. As will be further described, the spinal jack designs described herein further permit adjustment, at any future time following initial surgical implantation, in a minimally invasive fashion and in order to re-adjust the spatial positioning established between the upper and lower halves of each variant of the spinal jack, such as in order to compensate and correct for downstream vertebral complications following the initial implantation of the spinal jack.

Referring again to FIG. 1, the perspective view of the spinal jack according to one non-limiting variant includes first 12 and second 14 bodies, also hereinafter referred to as spinal jack halves, which are shown in a retracted position prior to being installed between succeeding superior articular processes associated with upper and lower consecutive spinal vertebra. Each of the spinal jack halves can be constructed of a suitable medical grade sanitary metal, plastic or composite and can incorporate opposite and outwardly facing gripping portions, these as further shown exhibiting a substantially ⊔U⊔ shape with aligning apertures configured in spaced apart and extending legs (see pairs 16/18 for each of first or upper jack half 12 and further at 20/22 for second or lower half 14).

Figure 1:
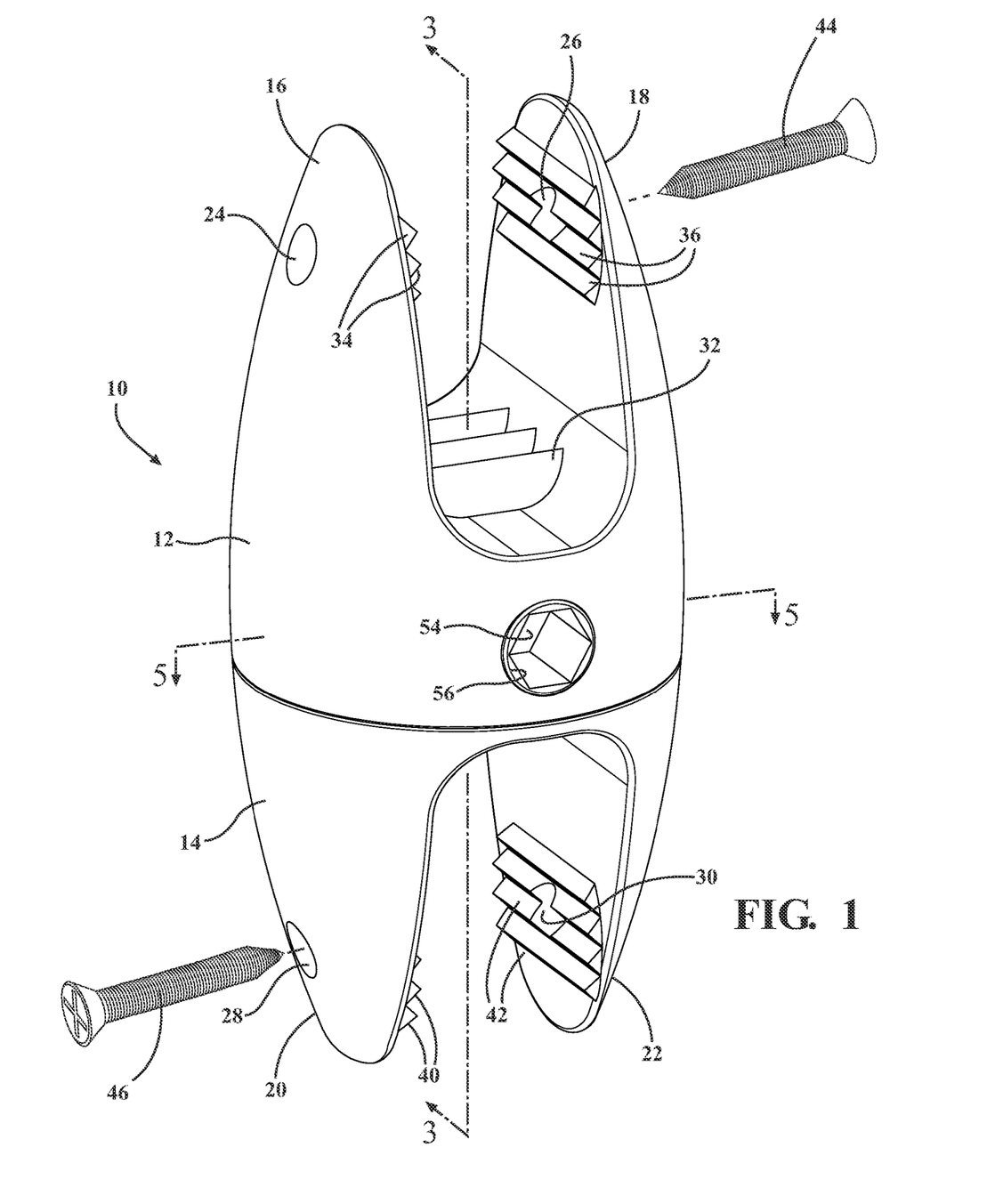
FIG. 1 is perspective view of a spinal jack according to one non-limiting variant and having first and second spinal jack halves shown in a retracted position prior to being installed between succeeding superior articular processes associated with upper and lower consecutive spinal vertebra.

Aligning apertures are further defined by spaced apart pairs of inner perimeter extending edges (at 24/26 for upper gripping portion legs 16/18 and at 28/30 for lower gripping portion legs 20/22). As understood, the spaced apart pairs of legs 16/18 and 20/22 of the opposite extending gripping portions are adapted to seat the upper and lower consecutive superior articular processes, The inner ▯U▯ shaped surface profile of each of the gripping portions is further exhibited by any type of textured or ribbed profile (see at inner base surface 32 and inner side surfaces 34/36 for the upper spinal jack gripping portion as well as inner base surface 38 and inner side surfaces 40/42 for the lower spinal jack gripping portion) the purpose of which is to provide additional resistive engagement against the facet surfaces of the vertebral processes and.

Also shown are screw type fasteners 44 and 46 (see FIG. 1) which, upon positioning and the gripping portions and drilling through the vertebral processes, anchor the spinal jack halves 12/14 to the respective vertebrae. Alternatively, the gripping portions can be crimped into engagement with the vertebral processes without the use of separate screws.

Figure 2:
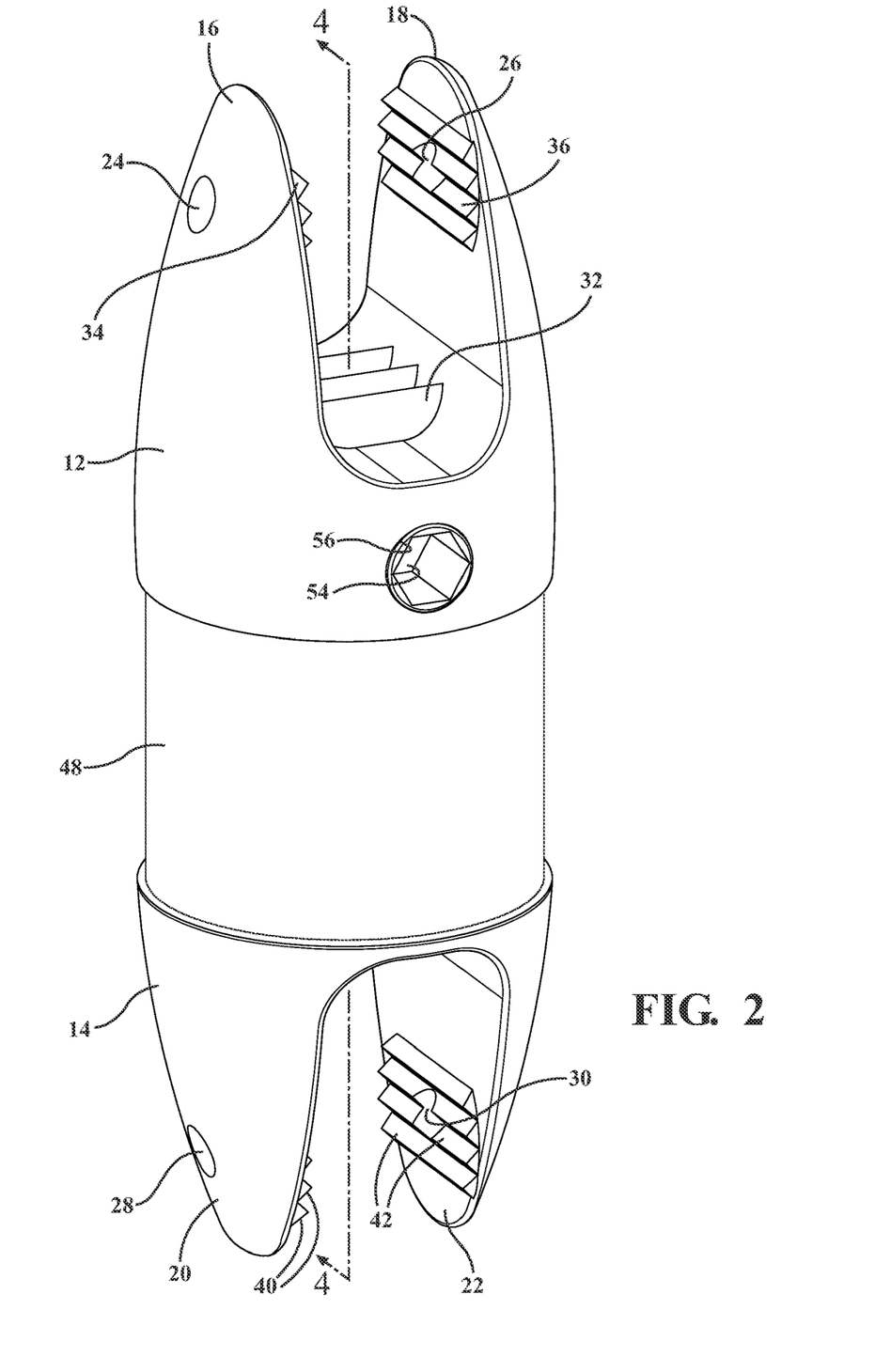
FIG. 2 is a succeeding illustration to FIG. 1 and depicting the spinal jack in an expanded position and further illustrating an expandable rubberized skirt located between the outwardly inter-displacing jack halves.

FIG. 2 is a succeeding illustration to FIG. 1 and depicts the spinal jack in an expanded position and further illustrating an expandable rubberized skirt 48 located between the outwardly inter-displacing jack halves 12/14. Without limitation, the skirt can be constructed of any suitable flexible and FDA (Food and Drug Administration) approved material.

Figure 3:
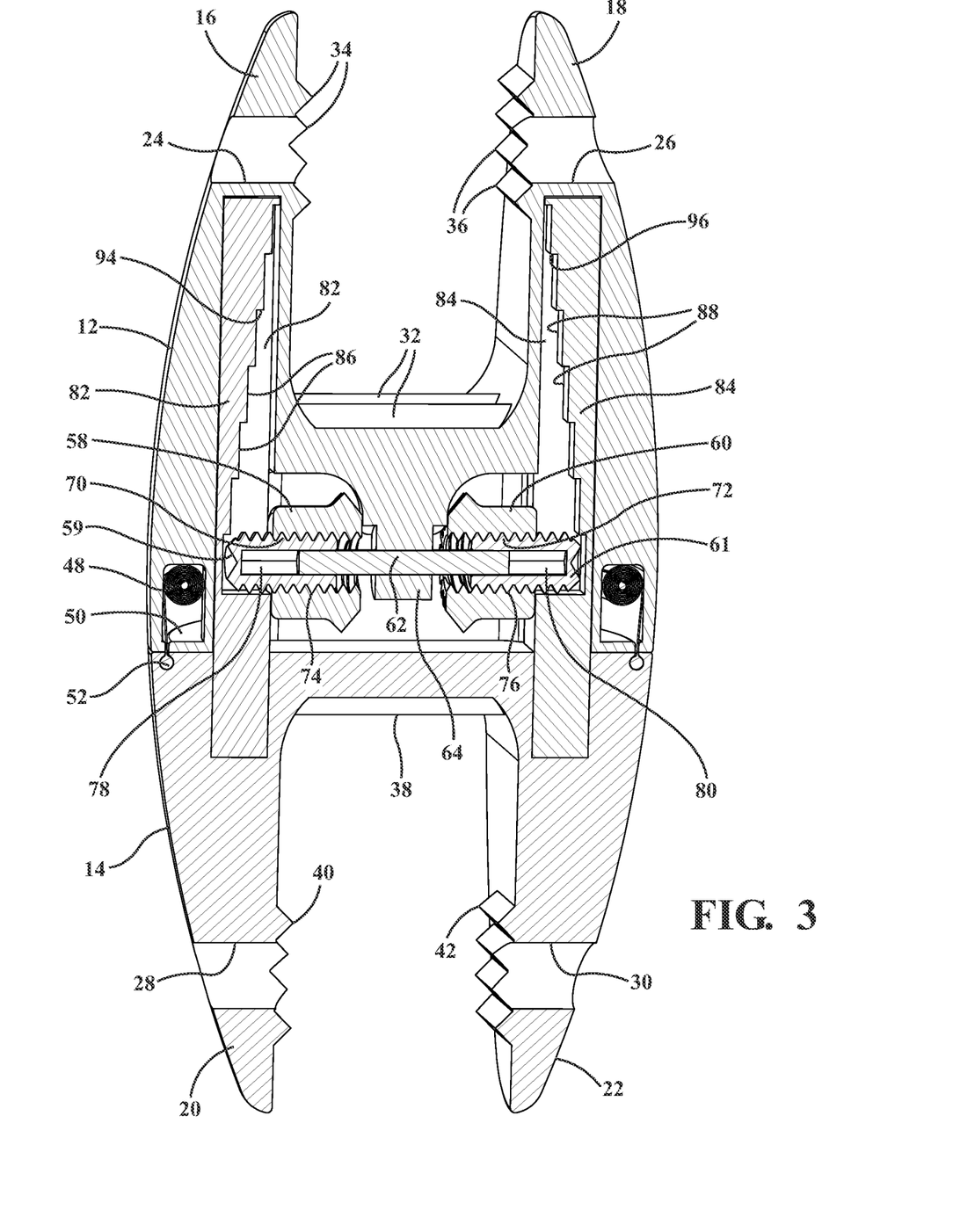
FIG. 3 is a cutaway view taken along line 3-3 of FIG. 1 and showing the pair of slave gears supported upon a width extending shaft in the retracted position.
Figure 4:
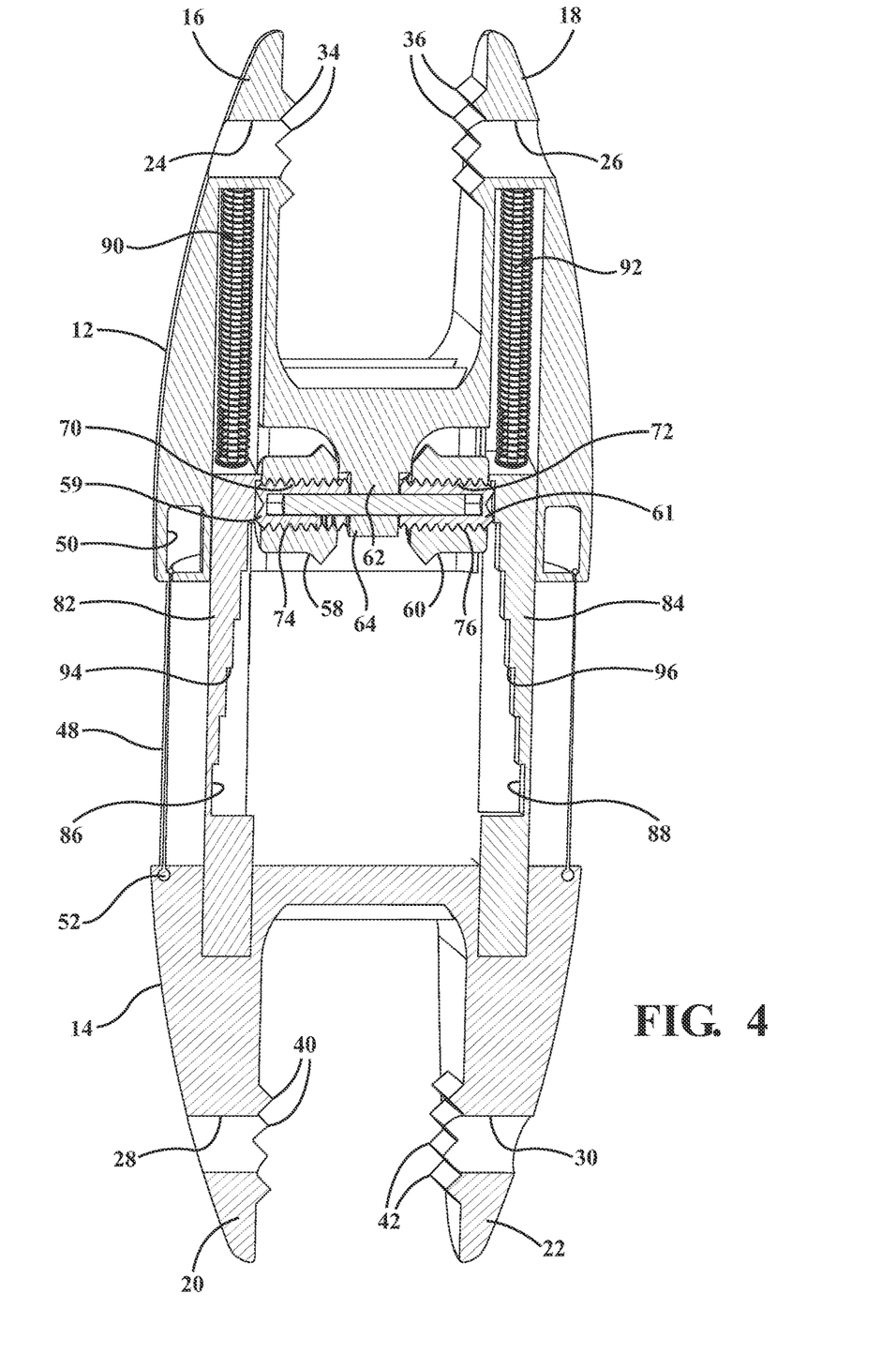
FIG. 4 is a cutaway view taken along line 4-4 of FIG. 2 and showing the adjusted position of the slave gears relative to the inwardly stepped ratchet stems to the outward-most expanded position.

As further best shown in the cutaway views of FIGS. 3-4, the skirt 48 is initially wound into a circumferential extending roll (FIG. 3) and seated within a likewise circumferentially extending pocket 50 extending within a base circumference of the upper spinal jack half 12. An opposite end of the skirt is anchored (at 52) to an opposing perimeter end face location of the lower spinal jack half 14 such that, and upon expanding the jack halves 12/14 as shown in FIG. 4, the skirt 48 unrolls to the position depicted in FIGS. 2-4 in which it provides a barrier between the exterior environment and the inner gear mechanism (to be described below) of the vertebral jack assembly. Additionally, the skirt 48 can be tensioned to the rolled up position of FIG. 3 (such as through the use of additional torsional springs, bands or the like) in order to maintain a tensioned and taut arrangement of the skirt at any expanded adjusted position established between the jack halves 12/14.

A rotatable driver component (see at 53 in FIG. 5) is depicted and includes an integrated hex head or other suitable bit receiving opening (further at 54). The driver component is further seated within a closed rim surface defining aperture 56 (see FIGS. 1, 2 and 5) associated with the first or upper jack half 12. A pair of laterally expandable slave gears 58 and 60 (see again FIGS. 3-5) are supported upon a width supported shaft 62, this in turn being secured in extending fashion through a lower interior projection 64 of the upper jack half 12.

Figure 5:
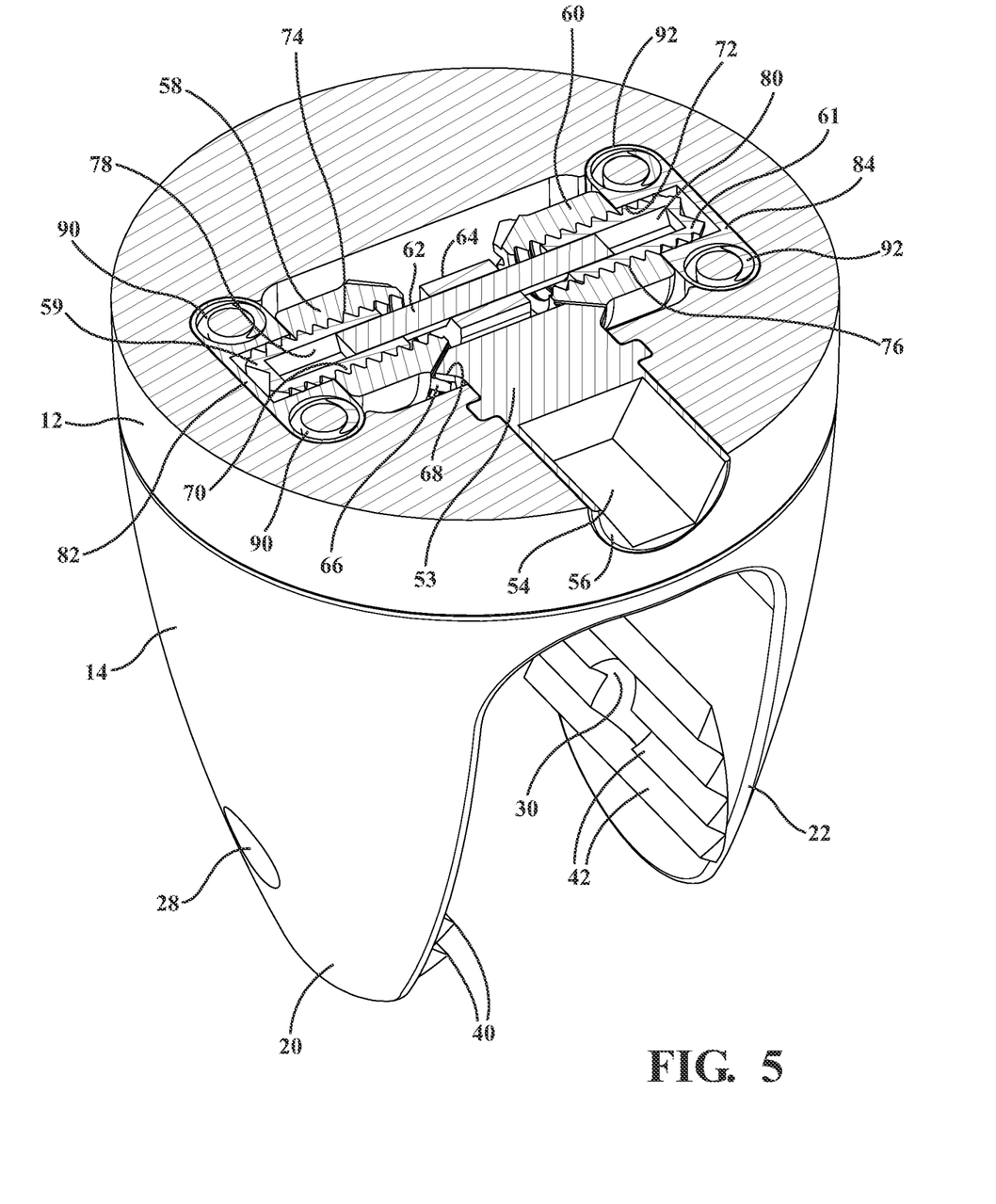
FIG. 5 is a cutaway taken along line 5-5 of FIG. 1 and showing bevel gear arrangement established between the drive gear and slave gears corresponding to the lowermost retracted position of FIG. 3.

As best shown in FIG. 5, a bevel gear arrangement is established between the driver component 53 and the slave gears 58/60. The slave gears 58/60 are stationary and each in turn further includes an interior and laterally displacing inner component (see at 59/61) which is threaded and inter-displaceable relative to the outer driving slave gears 58/60. The inner components 59/61 are further seated, as shown, over opposite ends of the stationary shaft 62 between the positions of FIG. 3 (retracted) and FIG. 4 (expanded).

FIG. 5 best shows bevel engaging tooth 66 (associated with selected slave gear 58) and corresponding outer bevel tooth 68 (associated with driver component 53), such that rotation of the hex head driver opening 54 (via the inserted bit) results in threaded engagement between interior threads 70 and 72 associated with each of the slave gears 58/60 and opposing exterior threaded locations 74 and 76 associated with each of the inner displacing components 59/61. The inner components 59/61 each further define interior channels (see as best shown at 78/80 in each of FIGS. 3 and 5) within which is seated the width supported and stationary shaft 62.

A pair of extending support stems 82 and 84 are associated with one of the jack halves, and which is shown in the FIGS. 3-4 cutaway views being anchored into the lower jack half 14 so that the stems 82/84 (best shown in FIG. 3) project upwardly within interior tracks or pockets 86/88 defined in the upper jack half 12. Each of the stems 82/84 include an individual plurality of opposing and progressively inwardly stepped ratchet locations (see at 86 for stem 82 and at 88 for stem 84 and which, without limitation, can be spaced at any desired incremental distance such as 2 mm per step) which abut the opposite outward faces of the laterally displacing inner components 59/61 and to assist in adjusting a lateral separation between the jack halves. One or more springs (see first pair 90 and second pair 92) are seated within the pocket shaped tracks or pockets 82/84 so that they are compressed/obscured in the retracted view of FIG. 3 (these can without limitation seat within upper end recessed locations defined in the ratchet stems 82/84).

In use, the inner displacing components 59/61 are depicted in the outermost displaced locations along the shaft 62 in the retracted position of FIG. 3. At this point, the spinal jack 10 is position in relation to a pair of succeeding superior articular processes and, upon actuating the rotary driving (e.g. hex key) component 53 in a first selected direction, the inter-threaded relationship with the slave gears 58/60 causes the inner components 59/61 to retract inwardly, to the point at which it unseats/inwardly clears in succession from each inwardly facing and opposing pair of progressively inwardly stepped ratchet locations 86/88. As each inward facing pair of stepped locations is cleared, the springs 90/92 progressively and outwardly expand the spinal jack halves 12/14 to each succeeding pair of stepped ratchet locations, and which can occur up to the last and inwardly-most stepped pair of opposing ratchets as shown in FIG. 4.

Once the spinal jack halves 12/14 are progressively expanded to the desired separation distance, the rotary driver component 53 is reverse rotated in a second direction to outwardly expand the inner components 59/61 in order to engage the desired pair of ratchet. Given the inwardly stepped nature of the ratchets, the desired expansion position between the spinal jack halves is maintained via the shoulder interfaces (see by example at 94/96) established between each succeeding pair of ratchets 86/88 so that, and upon outwardly tightening the inner components 59/61 of the slave gears 58/60 at the desired ratchet locations 86/86, the adjoining shoulders 94/96 corresponding to the next inwardly stepped ratchet location provide a secure engagement profile and prevent further inter expansion of the spinal jack halves 12/14.

Figure 6:
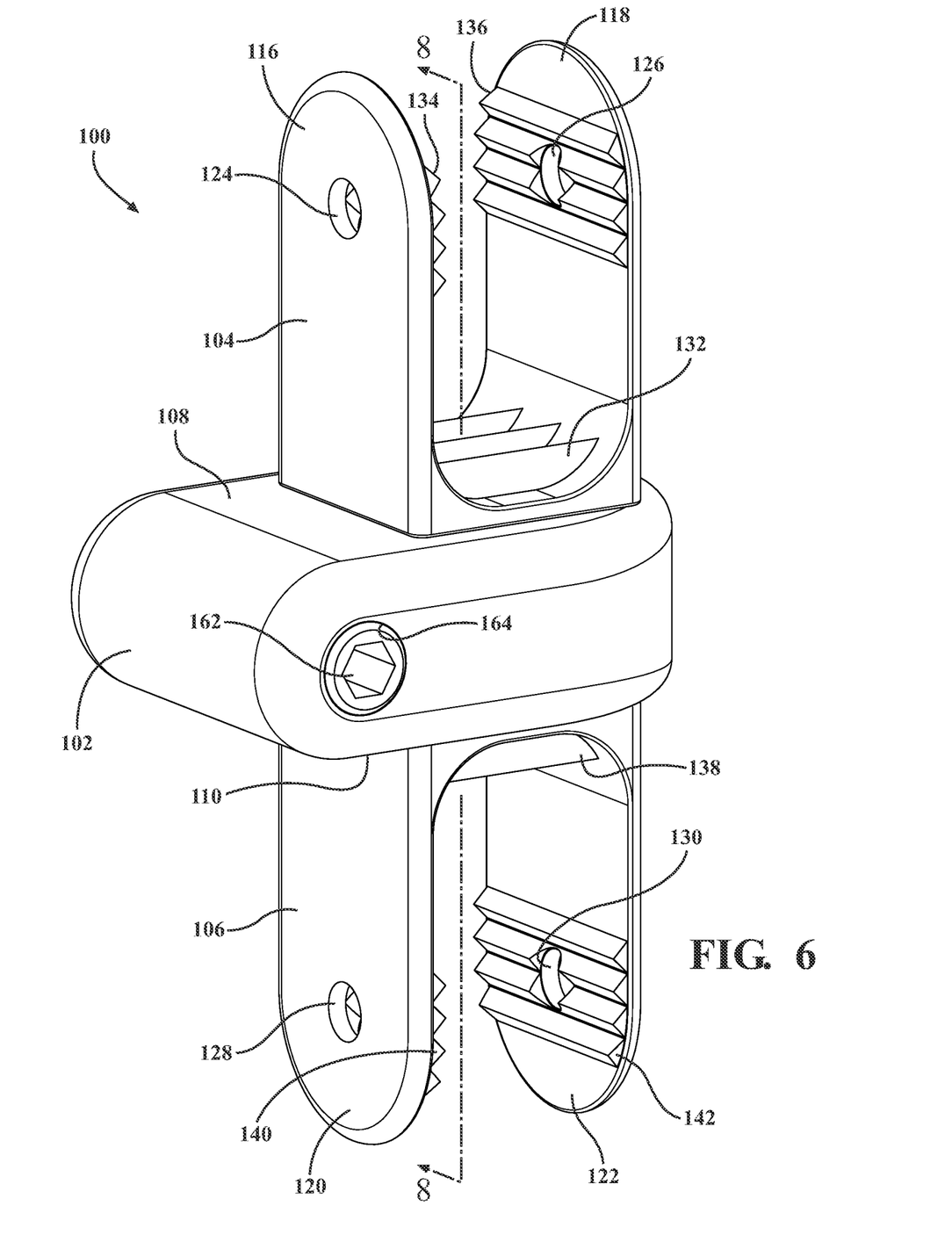
FIG. 6 is a perspective view of a spinal jack according to a further non-limiting variant and including a central body supports the outwardly displaceable spinal jack halves in a retracted position.

Proceeding now to FIG. 6 is a perspective view of a spinal jack is generally shown at 100 according to a further non-limiting variant in a retracted position and includes a central body 102 which supports a pair of outwardly displaceable spinal jack halves 104 and 106, each of which again including any medical grade metal, plastic or composite material.

The central body 12 (as best shown in the spinal jack expanded position of FIG. 7) depicts a three dimensional modified puck shape with top 108 and bottom 110 facing surfaces, against which are seated (in the retracted positions of FIGS. 6 and 8) base surfaces 112 and 114 associated with gripping portions configured into each of the upper 102 and lower 104 jack halves.

Similar to the preceding embodiment 10 of FIG. 1, the gripping portions each further exhibit a substantially "U" shape with aligning apertures configured in spaced apart and extending legs (see upper pairs 116/118 and 120/122 for each gripping portion associated with the upper 102 and lower 104 spinal jack halves). The aligning apertures are further defined by spaced apart pairs of inner perimeter extending edges (at 124/126 for upper spaced apart legs 116/118 and further at 128/130 for lower spaced apart legs 120/122).

With reference again to FIG. 1, the spaced apart pairs of legs 116/118 and 120/122 of the opposite extending gripping portions are adapted to seat the upper and lower consecutive superior articular processes, The inner "U" shaped surface profile of each of the gripping portions is further exhibited by any type of textured or ribbed profile (see at inner base surface 132 and inner side surfaces 134/136 for the upper gripping portion as well as inner base surface 138 and inner side surfaces 140/142 for the lower gripping portion) the purpose of which is to provide additional resistive engagement against the facet surfaces of the processes. As shown at 44 and 46 in FIG. 1, any type of screw fasteners can be employed and which, upon pre-positioning the gripping portions and drilling through the processes, anchor the jack halves 12/14 to the respective vertebrae. Alternatively, and as previously stated, the gripping portions can be crimped into engagement with the vertebral processes without the use of separate screws.

Figure 7:
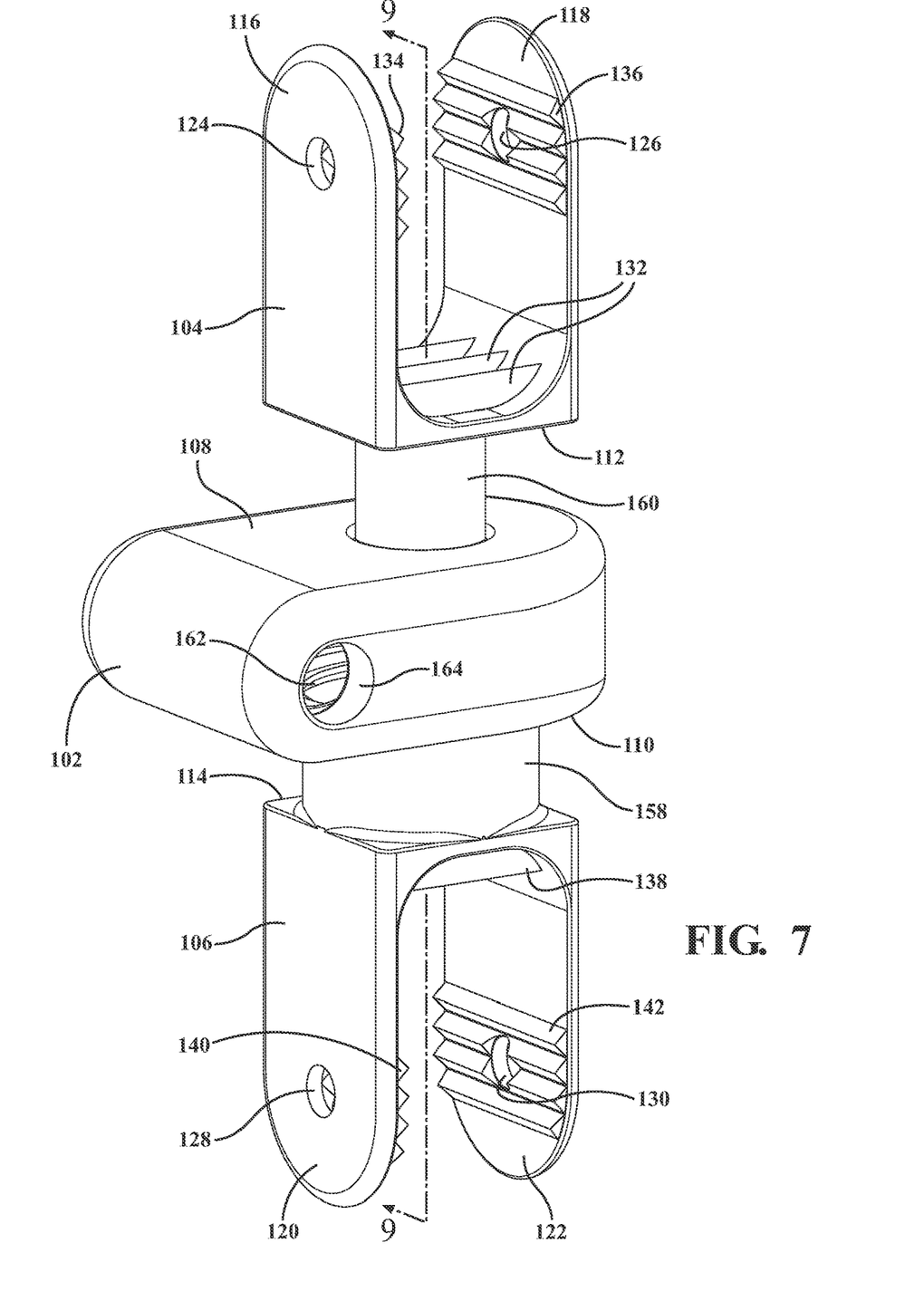
FIG. 7 is a further view to FIG. 6 and illustrating the spinal jack halves in an inter-outward expanded position.
Figure 8:
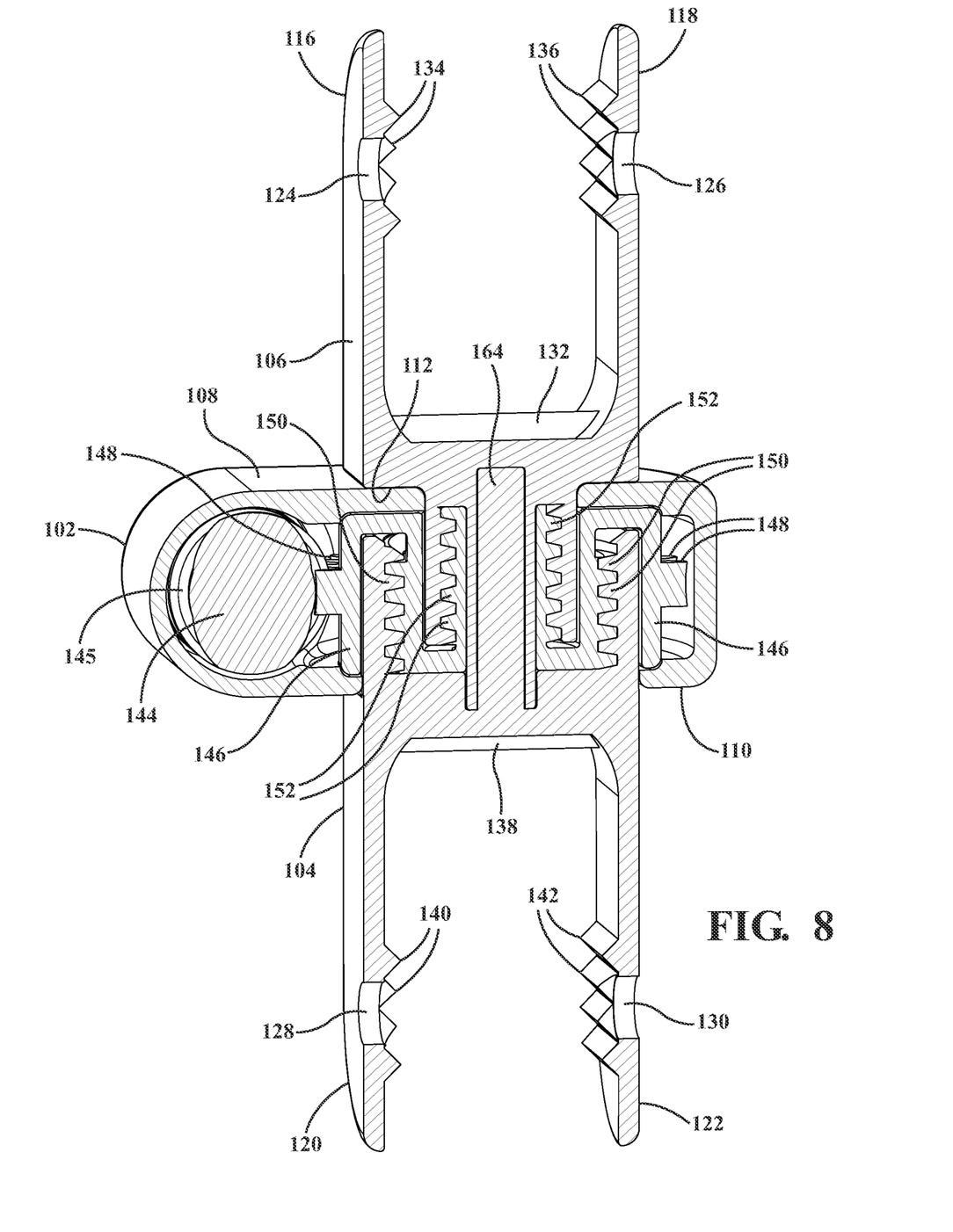
FIG. 8 is a cutaway view taken along line 8-8 of FIG. 6 and illustrating the rotatable worm gear which in turn actuates a disk gear having both outer and inner coaxial arranged teeth, these in turn meshing with opposing teeth configured in the support stems associated with each of the jack halves.
Figure 9:
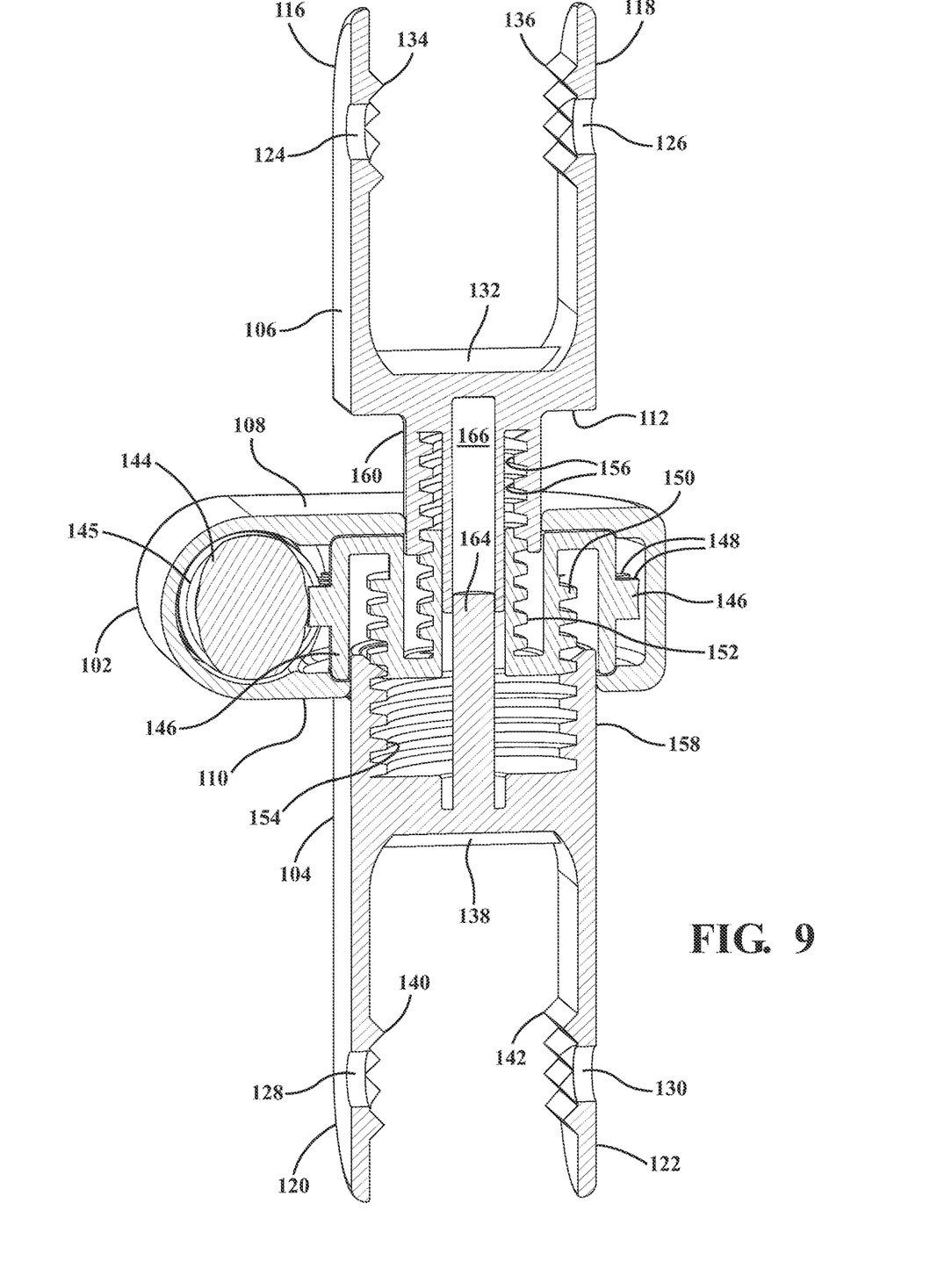
FIG. 9 is a corresponding cutaway view to FIG. 8 and depicting the spinal jack halves being caused to inter-displace in the outwardly expanding configuration.

FIG. 7 is a further view to FIG. 6 and illustrating the spinal jack halves 12/14 in an inter-outward expanded position. FIG. 8 further provides a cutaway view taken along line 8-8 of FIG. 6 and illustrating the rotatable worm gear which in turn actuates a disk gear having both outer and inner coaxial arranged threads, these in turn meshing with threads configured in support stems associated with each of the jack halves. FIG. 9 is a cutaway view similar to FIG. 8 and depicting the spinal jack halves 12/14 being caused to inter-displace in the outwardly expanding configuration.

As best shown in FIGS. 8-9, the central body 102 includes a rotatable worm gear 144 having exterior spiral arrayed teeth 145 and which, in turn, actuates a disk gear 146, this further exhibiting a multi-sided profile as depicted in cutaway and having both outer most facing annular threads or spiral teeth 148, along with each of first 150 and second 152 coaxially arranged inner threads or teeth. These in turn mesh with opposing coaxial threads or teeth 154 and 156 (see further as best shown in FIG. 9) configured in in each of support stems 158 (lower spinal jack 14) and 160 (upper spinal jack 12) and so that, upon actuating the worm gear 144 to drive the disk gear 146, the spinal jack halves are caused to inter-displace in an outwardly expanding configuration.

Similar to the first variant, a hex or other bit shaped key insert portion 162 is shown which is seated within a closed rim 164 defining an access passageway through the central body 12. Although not shown, the bit portion 162 can be integrated into the worm gear 144 for inter-displacing the spinal jack halves 12/14 in the manner shown between FIGS. 8-9.

Owing further to the inter-engaging geared relationship established between the worm gear 144, rotatably engaged disk gear 146 and opposing threaded gears 154/156 associated with the inner support stems 158 and 160 of the jack halves 14/12, adjustment of the spinal jack halves is provided in a secured fashion (such as during either of initial implantation or in response to a subsequent change in the patient s condition in which the spinal jack is further adjusted in-situ and without removing from the vertebral superior processes). Additional structural features can include an inner-most stem 164, shown integrated into the lower support stem 158 of the lower jack half 106, which seats within an aligning inner-most pocket 166 (see FIG. 9) defined in the upper support stem 160 of the upper jack half 104 and in use provides secure support to the jack halves in their inter-expanded outer configuration of FIGS. 7 and 9.

Having described my invention, other and additional preferred embodiments will become apparent to those skilled in the art to which it pertains, and without deviating from the scope of the appended claims. The detailed description and drawings are further understood to be supportive of the disclosure, the scope of which being defined by the claims. While some of the best modes and other embodiments for carrying out the claimed teachings have been described in detail, various alternative designs and embodiments exist for practicing the disclosure defined in the appended claims.

The foregoing disclosure is further understood as not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, a person of ordinary skill in the art will recognize that changes may be made in form and detail without departing from the scope of the present disclosure. Thus, the present disclosure is limited only by the claims.

In the foregoing specification, the disclosure has been described with reference to specific embodiments. However, as one skilled in the art will appreciate, various embodiments disclosed herein can be modified or otherwise implemented in various other ways without departing from the spirit and scope of the disclosure. Accordingly, this description is to be considered as illustrative and is for the purpose of teaching those skilled in the art the manner of making and using various embodiments of the disclosure. It is to be understood that the forms of disclosure herein shown and described are to be taken as representative embodiments. Equivalent elements, materials, processes or steps may be substituted for those representatively illustrated and described herein. Moreover, certain features of the disclosure may be utilized independently of the use of other features, all as would be apparent to one skilled in the art after having the benefit of this description of the disclosure. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural.

Further, various embodiments disclosed herein are to be taken in the illustrative and explanatory sense, and should in no way be construed as limiting of the present disclosure. All joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly.

Moreover, such joinder references do not necessarily infer that two elements are directly connected to each other.

Additionally, all numerical terms, such as, but not limited to, ▯first▯, ▯second▯, ▯third▯, ▯primary▯, ▯secondary▯, ▯main▯ or any other ordinary and/or numerical terms, should also be taken only as identifiers, to assist the reader's understanding of the various elements, embodiments, variations and/or modifications of the present disclosure, and may not create any limitations, particularly as to the order, or preference, of any element, embodiment, variation and/or modification relative to, or over, another element, embodiment, variation and/or modification.

It will also be appreciated that one or more of the elements depicted in the drawings/figures can also be implemented in a more separated or integrated manner, or even removed or rendered as inoperable in certain cases, as is useful in accordance with a particular application. Additionally, any signal hatches in the drawings/figures should be considered only as exemplary, and not limiting, unless otherwise specifically specified.

The invention claimed is:

1. A spinal jack adapted for installation between first and second vertebral processes, comprising:
    an upper spinal jack body and a lower spinal jack body, each of said bodies including gripping portions adapted for engaging the vertebral processes;
    a rotatable and geared driver incorporated into one of said bodies and engaging a pair of beveled slaved gears; and
    said slaved gears further including inner displaceable portions, opposing threads being established between said slaved gears and said inner displaceable portions which, upon rotation of said slaved gears, laterally displacing said inner portions to engage opposing and progressively stepped ratchet locations configured into stems extending between said bodies to define an adjusted separation distance between said bodies.

2. The spinal jack as described in claim 1, said gripping portions each further comprising a pocket adapted to receive the vertebral process there between.

3. The spinal jack of claim 2, said pockets each further including textured surfaces for providing additional gripping of the vertebral processes.

4. The spinal jack of claim 1, further comprising each of said upper and lower bodies further comprising any medical grade sanitary metal, plastic or composite material.

5. The spinal jack of claim 1, each of said gripping portions further comprising a substantially "U" shape with aligning apertures configured in spaced apart and extending legs for receiving screw fasteners for securing said gripping portions to the vertebral processses.

6. The spinal jack of claim 1, further comprising an expandable rubberized skirt extending between said spinal jack bodies.

7. The spinal jack of claim 6, further comprising said skirt being initially wound into a circumferential extending roll and seated within a likewise circumferentially extending pocket extending within a base circumference of said upper spinal jack body, an opposite end of said skirt anchored to an opposing perimeter end face location of said lower spinal jack body such that, and upon expanding said jack bodies, said skirt unrolls to provide a barrier between an exterior environment and said gears.

8. The spinal jack of claim 1, further comprising said inner displaceable portions seated upon opposite ends of a stationary interior shaft supported upon a lower interior projection of the other of said bodies.

9. The spinal jack of claim 1, further comprising interior pockets in the other of said jack bodies, one or more outward biasing springs seated within said pockets for biasing said stems and jack bodies in an expanding direction restrained by said inner portions engaged to said ratchet locations.

10. A spinal jack adapted for installation between first and second vertebral processes, comprising:
    an upper spinal jack body and a lower spinal jack body, each of said bodies including gripping portions adapted for engaging the vertebral processes;
    a rotatable and geared driver incorporated into one of said bodies and engaging a pair of beveled slaved gears, a pair of inner portions of said slaved gears being laterally outwardly displaced into engagement with stems extending between said bodies to define an adjusted separation distance; and
    a rubberized skirt configured as a wound roll seated within a circumferentially extending pocket extending within a base circumference of one of said jack bodies when said jack bodies are in a closed position, an opposite end of said skirt anchored to an opposing perimeter end face location in the other of said jack bodies such that, and upon expanding said jack bodies, said skirt unrolls to provide a barrier between an exterior environment and an expanding interior defined between said bodies.

11. The spinal jack of claim 10, further comprising opposing threads being established between said slaved gears and said inner displaceable portions which, upon rotation of said slaved gears, laterally displacing said inner portions to engage opposing and progressively stepped ratchet locations configured into stems extending between said bodies to define an adjusted separation distance between said bodies.

12. The spinal jack of claim 10, further comprising interior pockets in the other of said jack bodies, outward biasing springs seated within said pockets for biasing said stems and jack bodies in an expanding direction restrained by said inner portions engaged to said ratchet locations.

* * * * *